(12) United States Patent
Kim

(10) Patent No.: US 8,597,718 B2
(45) Date of Patent: Dec. 3, 2013

(54) CALCIUM PHOSPHATE ULTRATHIN FILMS AND A METHOD FOR PREPARING THEM

(75) Inventor: Hyun Man Kim, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 701 days.

(21) Appl. No.: 12/665,143

(22) PCT Filed: Jun. 20, 2008

(86) PCT No.: PCT/KR2008/003526
§ 371 (c)(1),
(2), (4) Date: Dec. 17, 2009

(87) PCT Pub. No.: WO2008/156332
PCT Pub. Date: Dec. 24, 2008

(65) Prior Publication Data
US 2010/0183858 A1    Jul. 22, 2010

(30) Foreign Application Priority Data
Jun. 20, 2007    (KR) ........................ 10-2007-0060645

(51) Int. Cl.
*B05D 1/36* (2006.01)
*C01B 25/32* (2006.01)

(52) U.S. Cl.
USPC ........................... 427/2.27; 423/308; 423/311

(58) Field of Classification Search
USPC ........................... 423/307, 308, 311; 427/2.27
See application file for complete search history.

(56) References Cited

U.S. PATENT DOCUMENTS

| | | | |
|---|---|---|---|
| 5,164,187 A * | 11/1992 | Constantz et al. | 424/423 |
| 6,069,295 A | 5/2000 | Leitao | |
| 6,153,266 A * | 11/2000 | Yokogawa et al. | 427/419.1 |
| 6,544,290 B1 | 4/2003 | Lee | |
| 6,596,338 B2 * | 7/2003 | Scott et al. | 427/2.26 |
| 6,720,023 B1 * | 4/2004 | Kim et al. | 427/2.27 |
| 6,977,095 B1 * | 12/2005 | Marx et al. | 427/2.26 |
| 7,344,749 B2 * | 3/2008 | Becker et al. | 427/2.1 |
| 7,648,728 B2 * | 1/2010 | Yamamoto et al. | 427/2.26 |
| 7,785,648 B2 * | 8/2010 | Rohanizadeh et al. | 427/2.1 |

FOREIGN PATENT DOCUMENTS

| | | |
|---|---|---|
| JP | 2007-075486 A | 3/2007 |
| KR | 10-2002-0017088 A | 3/2002 |
| KR | 10-2002-0018696 A | 3/2002 |
| WO | WO 2008/156332 A1 | 12/2008 |

* cited by examiner

*Primary Examiner* — Wayne Langel
(74) *Attorney, Agent, or Firm* — Joseph H. Kim; JHK Law

(57) ABSTRACT

An ultrathin film of calcium phosphate crystals having a thickness of 200 nm or less on a surface of a solid substrate, and a method for preparing the same are disclosed. Further, an amorphous dendritic extension used as an intermediate material in preparation of the ultrathin film of calcium phosphate and a method for forming the same are disclosed. The ultrathin film of calcium phosphate crystals can be coated on the surface of the solid substrate while substantially maintaining surface roughness of the solid substrate. The method employs calcium phosphate ion solutions at low temperature. The ion solutions are separately applied to the steps of 1) forming granules of amorphous calcium phosphate on a surface of a solid substrate, 2) forming a dendritic precursor matrix of surface crystals around the granule of amorphous calcium phosphate, 3) removing the amorphous granule via dissolution before the amorphous granule is crystallized, and 4) crystallizing the dendritic precursor matrix of surface crystals to form surface crystals and multiplicating the crystals over the surface of the solid substrate, thereby forming an ultrathin film of calcium phosphate crystals having a thickness of 200 nm or less.

14 Claims, 7 Drawing Sheets

CALCIUM PHOSPHATE ULTRATHIN FILMS AND A METHOD FOR PREPARING THEM

TECHNICAL FIELD

The present invention relates to an ultrathin film of calcium phosphate crystals and a method for preparing the same. More particularly, the present invention relates to an ultrathin film of calcium phosphate crystals having a thickness of 200 nm or less and capable of being coated on the surface of a solid substrate while substantially maintaining surface roughness of the solid substrate, and a method for preparing the same. Further, the present invention relates to an amorphous dendritic extension used as an intermediate material for preparation of the ultrathin film of calcium phosphate crystals having a thickness of 200 nm or less, and a method for forming the same.

BACKGROUND ART

Calcium phosphates are present in teeth and bone constituting the skeleton of vertebrate animals including humans (H.-M. Kim et al., *J. Bone Miner. Res.* Vol. 10, 1589-1601 (1995); U.S. Pat. No. 5,565,502; and U.S. Pat. No. 5,691, 397). Calcium phosphate crystals have been known as biomaterials that can be used as stable substitutes for bone due to biocompatibility thereof. Further, calcium phosphates exhibit a high adsorptivity with respect to organic or inorganic ions and molecules, and thus have applications including adsorption of heavy metal ions, deodorization, adsorption of microorganisms such as viruses, and the like (M. Peld et al., *Environ. Sci. Technol.* 38, 5626-5631 (2004); Q. Y. Ma et al., *Environ. Sci. Technol.* 27, 1803-1810 (1993); H. Tanaka et al., *Arch. Oral Biol.* 41, 505-508 (1996); S. Tsuru et al., *Biomed. Mater. Eng.* 1, 143-147 (1991)). Calcium phosphates are prepared in a variety of shapes including a bar shape, a thorn shape, a flake shape, granules shape, a thin film shape, etc., and are widely used as biomaterials, heavy metal adsorption agents, deodorization agents, and the like.

DISCLOSURE

Technical Problem

A calcium phosphate thin film can be coated on the surface of a solid substrate for the purpose of achieving useful biological, physical, and chemical reactivity of calcium phosphate without causing variation of inherent mechanical properties of the solid substrate. Via this coating process, it is possible to develop high performance materials which combine various shapes and physical properties of metals or polymers and the high reactivity of calcium phosphate.

However, the thickness of the calcium phosphate film has a great influence on the performance of the calcium phosphate thin film. Namely, an increase in the thickness of the calcium phosphate film causes the calcium phosphate film to be more easily damaged by external mechanical impact and negates effect of irregularities formed on the surface of the solid substrate under the film. The irregularities on the surface of the solid substrate are not only directly related to the surface area of the solid substrate that has influence on adsorption efficiency, but also have a great influence on cell and tissue reaction to the biomaterial (S. A. Hacking et al., *Clin. Orthop Relat. Res.* 405, 24-38 (2002); D. Perrine et al., *Clin. Oral Implants Res.* 13, 465-469 (2002)). Accordingly, it is desirable that the thickness of the calcium phosphate film be as thin as possible while still being capable of withstanding stress applied to the film without negating the effects of minute irregularities on the surface of the solid substrate under the film.

However, since a conventional thin film of calcium phosphate is several micrometers or more thick, not only does the thin film negate the effects of the irregularities, but also tends to be broken due to mechanical impact. Therefore, there is a need for an ultrathin film of calcium phosphate crystals that has a very small thickness in a nanometer scale to improve physical and chemical characteristics, and biological reactivity.

The preparation of calcium phosphate thin film starts with preparation of a calcium phosphate ion solution. The calcium phosphate ion solution is prepared by selecting compounds from all compounds comprising $Ca^{2+}$ and $PO_4^{3-}$. Here, one example of compounds comprising $Ca^{2+}$ ions can be selected from $Ca(NO_3)_2 \cdot 4H_2O$, $CaCl_2$, etc. One example of compounds comprising $PO_4^{3-}$ ions can be selected from $Na_2HPO_4 \cdot 2H_2O$, $NaH_2PO_4 \cdot H_2O$, $K_2HPO_4 \cdot 3H_2O$, and $KH_2PO_4$, etc. Typically, the calcium phosphate thin film can be prepared using a supersaturated solution of high concentration calcium phosphate (Hyun-Man Kim, Jea-Seung Ko, Yoon-Jin Kim, Soo-Jin Park, Korean Patent No. 0353141; and Hyun-Man Kim, Jea-Seung Ko, Korean Patent No. 0511338). However, the conventional method fails to adjust the thickness of the thin film, so that the thin film has a thickness in the range of 500 nm~several micrometers.

Technical Solution

The present invention is conceived to solve the problems of the conventional techniques as described above, and developed based on new knowledge as to the preparation of a thin film of calcium phosphate crystals on the surface of a solid substrate. That is, the thin film of calcium phosphate crystals is prepared by 1) forming granules of amorphous calcium phosphate on the surface of a solid substrate, 2) growing an amorphous dendritic extension as a precursor matrix of surface crystals from the granule of amorphous calcium phosphate in contact with the surface of the solid substrate, 3) crystallizing both the amorphous dendritic extension and the amorphous granule on the surface of the solid substrate, and 4) multiplicating the crystals to coat the surface of the solid substrate with calcium phosphate crystals. Here, the solubility of the amorphous dendritic extension, which is adhered as the precursor matrix of surface crystals to the surface of the solid substrate, is lower than that of the amorphous granule. Further, crystallization of the granule of amorphous calcium phosphate occurs after dendritic amorphous precursor matrix of surface crystals protrudes from the amorphous granule.

As such, the present invention prepares an ultrathin film of calcium phosphate by using the amorphous dendritic extension, that is, the precursor matrix of surface crystals, as an intermediate material for the preparation of the ultrathin film of calcium phosphate while removing the amorphous granule of calcium phosphate before crystallization of the amorphous granule of calcium phosphate but after formation of the amorphous dendritic extension. Further, the present invention prepares the ultrathin film of calcium phosphate by adjusting the formation of the surface crystals based on the characteristics that the amorphous dendritic extension as the precursor matrix of surface crystals has a lower solubility than the amorphous granule of calcium phosphate, and that crystallization of the amorphous granule of calcium phosphate occurs after the formation of the amorphous dendritic precursor matrix of the surface crystal. In other words, the amorphous granule is removed via dissolution before crystallization of the amorphous granule but after the formation of the amorphous dendritic extension on the surface of the amorphous granule, so that the amorphous granule does not affect formation of a surface crystal layer and the crystals on the surface are formed only from amorphous dendritic precursor matrix of the surface crystals thinly adhered to the surface of the solid substrate as the intermediate material of the crystals to produce the ultrathin crystal layer.

In brief, the preparation of the ultrathin film of calcium phosphate crystals includes: 1) forming the granule of amorphous calcium phosphate on the surface of a solid substrate, 2) forming a dendritic matrix of surface crystals around the granule of amorphous calcium phosphate, 3) removing the amorphous granule via dissolution before the amorphous granule is crystallized, and 4) crystallizing the dendritic precursor matrix of surface crystals and multiplicating the surface crystals over the surface of the solid substrate. At this time, each of the steps can be adjusted to achieve the preparation of the ultrathin film of calcium phosphate crystals according to the invention. Since the preparation of thin film of calcium phosphate crystals is conventionally carried out by a series of consecutive processes without dividing the total process into the steps as described above, the previously known thin films of the calcium phosphate crystals have a great thickness. However, according to the present invention, the preparation of the thin film of calcium phosphate crystals using the calcium phosphate ion solution is divided into the several steps at novel conditions, thereby achieving the above and other objects of the present invention.

Among the aforementioned four steps in formation of the ultrathin film of calcium phosphate, the step of removing the granule of amorphous calcium phosphate formed in step 1) is important since it has a great influence on the thickness of the thin film of calcium phosphate. If the granule is converted into crystals, the calcium phosphate crystals are thickly grown on and around the granule, causing an increase in thickness of the calcium phosphate thin film. Accordingly, in order to reduce the thickness of the calcium phosphate thin film, the amorphous granule of calcium phosphate is removed before crystallization thereof. It is also possible to prepare the ultrathin film of calcium phosphate crystals without removing the amorphous granule of calcium phosphate if a very fine amorphous granule having a similar size to that of the crystals is formed. The amorphous granule is converted into a planar crystal adhered to the surface of the solid substrate instead of a crystalline globule to produce the ultrathin film of calcium phosphate. However, when the granule is converted into a spherical crystal, the crystal can be thickly grown around the granule except for the case where the amorphous granule does not have an ultrafine size. Thus, when the amorphous granule is not ultrafine, it is desirable to remove as much of the amorphous granule as possible.

Next, the method for preparing an ultrathin film of calcium phosphate crystals according to the present invention will be described in detail.

1) Preparation of a Calcium Phosphate Ion Solution

According to one embodiment of the present invention, a calcium phosphate ion solution prepared by a conventional method (Hyun-Man Kim, Jea-Seung Ko, Korean Patent No. 0511338) is used to adjust respective steps in the preparation of the ultrathin film of calcium phosphate crystals. In other words, according to the present invention, the calcium phosphate ion solution is adjusted in concentration and used several times according to the purposes of using the calcium phosphate ion solution. The calcium phosphate ion solution is used for four purposes as follows.

Calcium phosphate ion solution 1: calcium phosphate ion solution used for forming granules of amorphous calcium phosphate having a diameter of 20 nm or less on the surface of a solid substrate having a high surface energy, such as metal, glass, ceramics, hydrophilic polymer, and hydrophilic tissues of animals and plants, or used for forming granules of amorphous calcium phosphate having a diameter of 400 nm or less on the surface of a solid substrate having a low surface energy such as a hydrophobic polymer. This calcium phosphate ion solution has an ion concentration product of $1\sim25$ mM$^2$.

Calcium phosphate ion solution 2: calcium phosphate ion solution used for forming dendritic amorphous precursor matrix of surface crystals around the granule of amorphous calcium phosphate. This calcium phosphate ion solution has an ion concentration product of $1\sim25$ mM$^2$.

Calcium phosphate ion solution 3: calcium phosphate ion solution used for dissolving the granule of amorphous calcium phosphate without dissolving dendritic amorphous precursor matrix of surface crystals. This calcium phosphate ion solution has an ion concentration product of $0.16\sim1$ mM$^2$.

Calcium phosphate ion solution 4: calcium phosphate ion solution used for converting dendritic amorphous precursor matrix of surface crystals into crystals and growing the crystals. This calcium phosphate ion solution has an ion concentration product of $1\sim64$ mM$^2$.

These calcium phosphate ion solutions are prepared by the steps of:

(1) preparing an ion solution containing phosphate ions;
(2) preparing an ion solution containing calcium ions; and
(3) mixing the ion solutions to prepare calcium phosphate ion solutions according to the respective concentration ranges.

Mixing the ion solutions in step (3) is performed at a temperature of 0~20° C., preferably maintained at a temperature of 0~10° C., and more preferably performed at the minimum temperature within this range at which formation of calcium phosphate precipitate does not occur. Further, to prevent the formation of the calcium phosphate precipitate due to a local increase in concentration, the mixing solutions may be distributed in small amounts and added at a low speed by means of solution stirring or other mechanical processes. The low speed addition of the mixing solution and stirring of the solution promote diffusion of added ions, thereby suppressing or delaying a local spontaneous formation of calcium phosphate compounds caused by a high concentration of the calcium phosphate solution.

According to the present invention, the use of a buffer solution is preferred to obtain a uniform solution of calcium phosphate during preparation of the calcium phosphate ion solution. The buffer solution may be an organic ion or inorganic ion buffer solution. The simplest composition can be obtained by using a phosphate buffer solution. Considering biocompatibility for a biomaterial, it is most preferable to use a phosphate buffer solution that has a simple composition and is prepared using only ions found in a living body.

According to the present invention, the calcium phosphate ion solution has a pH of 6.8~8.0, preferably a pH of 7.0~7.6, and more preferably a pH of 7.2~7.5.

2) Preparation of an Ultrathin Film of Calcium Phosphate

An ultrathin film of calcium phosphate having a thickness of 200 nm or less is prepared using the calcium phosphate ion solution prepared as described above.

The first embodiment of the present invention produces granules of amorphous calcium phosphate having a diameter of 400 nm or less on a solid substrate using calcium phosphate ion solution 1. Then, dendritic amorphous precursor matrix of surface crystals is formed around the granule of amorphous calcium phosphate using calcium phosphate ion solution 2. Next, the granule of amorphous calcium phosphate is removed using calcium phosphate ion solution 3 while allowing dendritic amorphous precursor matrix of calcium phosphate surface crystals to remain. Finally, crystallization of dendritic amorphous precursor matrix of calcium phosphate surface crystals and multiplication of the surface crystals are performed using calcium phosphate ion solution 4 on the surface of the solid substrate, so that an ultrathin film of calcium phosphate crystals having a thickness of 200 nm or less can be prepared on the solid substrate. In preparation of the ultrathin film of calcium phosphate crystals, the granule of amorphous calcium phosphate may have a diameter of 400 nm or less. Preferably, the granule of amorphous calcium phosphate may have a diameter of 100~400 nm, which provides a low surface energy not to delay the formation of dendritic amorphous precursor matrix of the surface crystals. The first embodiment can be applied to any hydrophilic or hydrophobic surfaces. However, with respect to a solid substrate having a water contact angle of 60 degrees or more and a lower surface energy, such as a hydrophobic polymer, and hydrophobic tissues of animals or plants, it is preferable to apply the first embodiment, since such a solid substrate allows the amorphous granule of calcium phosphate having an enlarged size to be formed at a low density thereon while delaying the formation of the amorphous dendritic matrix of the surface crystals.

More specifically, as a primary reaction, the granule of amorphous calcium phosphate having a diameter of 400 nm or less is formed using calcium phosphate ion solution 1 on the surface of the solid substrate. To form the granule of amorphous calcium phosphate on the surface of the solid substrate, the temperature of the ion solution is elevated. Temperature elevation is started at a temperature range of 0~30° C., and more preferably at a temperature range of 0~10° C. The temperature elevation is finished at a temperature range of 8~50° C. Here, the temperature is raised by at least 5° C. or more. After the granule is formed, the ion solution is removed, followed by rinsing with distilled water for 2~3 seconds to stop the reaction.

Then, as a secondary reaction, an amorphous dendritic extension is grown as the precursor matrix of the surface crystals from the granule of amorphous calcium phosphate using calcium phosphate ion solution 2 toward the surface of the solid substrate. In order to prevent formation of the dendritic precursor matrix of the surface crystals from occurring so rapidly that formation thereof cannot be regulated, and to prevent rapid crystallization of the dendritic precursor matrix of the surface crystals, it is preferable to lower the formation rate of the precursor dendritic matrix of the surface crystals by performing the reaction at as low a temperature as possible. However, if the reaction temperature is too low, the reaction rate becomes too low. Thus, the reaction temperature may be set to be a freezing point ~50° C., preferably to be 5~35° C., and more preferably to be 10~25° C. for a proper reaction rate. After the precursor dendritic matrix of the surface crystals is formed, the ion solution is removed, followed by rinsing with distilled water for 2~3 seconds to stop the reaction.

Next, while allowing the precursor dendritic matrix of the surface crystals to remain on the surface of the solid crystals, the granule of amorphous calcium phosphate is dissolved using calcium phosphate ion solution 3 to remove the granule of amorphous calcium phosphate, which can thicken the thin film during crystallization of the matrix. The reaction temperature may be set to be a freezing point~50° C., preferably to be 5~35° C., and more preferably to be 10~25° C. for a proper reaction rate.

Finally, crystallization of the dendritic precursor matrix of the surface crystals and multiplication of surface crystals are carried out using calcium phosphate ion solution 4, thereby preparing the ultrathin film of calcium phosphate crystals having a thickness of 200 nm or less on the solid substrate. At this time, to prepare the ultrathin film of calcium phosphate crystals having a thickness of 200 nm or less, it is necessary to keep the multiplication rate of the surface crystals low to control film thickness. For this purpose, this reaction is performed at as low a temperature as possible to allow the crystals to grow at a low multiplication rate. However, if the reaction temperature is too low, the reaction rate becomes too low. Thus, the reaction temperature may be set to be 5~50° C., preferably to be 5~35° C., and more preferably to be 10~25° C. for a proper reaction rate.

As the second embodiment of the present invention, both small granules of amorphous calcium phosphate having a diameter of 20 nm or less and a dendritic precursor matrix of surface crystals are formed on a solid substrate using calcium phosphate ion solution 1 as a primary reaction. Then, as a secondary reaction, both the granule of amorphous calcium phosphate and a dendritic precursor matrix of surface crystals are simultaneously treated with calcium phosphate ion solution 4, so that a thin film of calcium phosphate crystals can be formed to have a thickness of 200 nm or less on the solid substrate. A solid substrate having a higher surface energy produces the granules of a smaller diameter than a solid substrate having a lower surface energy, allows a greater amount of granules of amorphous calcium phosphate to be found at a higher rate thereto than the solid substrate having the lower surface energy. Furthermore, the solid substrate having the higher surface energy allows the dendritic precursor matrix of the surface crystals to be grown from the amorphous granule at a higher rate than the solid substrate having the lower surface energy. Therefore, it is possible to prepare the ultrathin film on the solid substrate having such a higher surface energy using the ion solution 4 without application of the ion solutions 2 and 3. In other words, the granule of amorphous calcium phosphate having a diameter of 20 nm or less is formed on the surface of the solid substrate using calcium phosphate ion solution 1, followed by formation and crystallization of a dendritic precursor matrix of surface crystals, dissolution or crystallization of the granule of amorphous calcium phosphate, and multiplication of the crystals using calcium phosphate ion solution 4, thereby preparing an ultrathin film of calcium phosphate having a thickness of 200 nm or less. The amorphous granule is removed before crystallization of the granule, or converted into crystals to be incorporated into the thin film. Since the amorphous granule is converted into the flat crystal and attached to the surface of the solid substrate instead of being converted into a large crystal globule due to the small size of the granule, it does not increase the thickness of the thin film even if it is not removed. The granule having the small size can be dissolved at an early stage by an ion solution which is acidified by calcium phosphate crystallization reaction. The second embodiment can be applied to any hydrophilic or hydrophobic surfaces. However, with respect to a solid substrate such as metal, glass, ceramics, hydrophilic polymer, and hydrophilic tissues of animals or plants having a water contact angle of 60 degrees or less and a high surface energy, it is preferable to apply the second embodiment since such a solid substrate allows the amorphous granule of calcium phosphate having a small size to be formed at a high density thereon.

More specifically, as the primary reaction, the granule of amorphous calcium phosphate having a diameter of 20 nm or less is formed using calcium phosphate ion solution 1 on the surface of the solid substrate. Then, after removing calcium phosphate ion solution 1, the amorphous granule are rinsed with distilled water for 2~3 seconds to stop the reaction. To form the granule of amorphous calcium phosphate on the surface of the solid substrate, the temperature of the ion solution is elevated. Temperature elevation is started at a temperature range of 0~30° C., and more preferably at a temperature range of 0~10° C. The temperature elevation is finished at a temperature range of 8~50° C. Here, the temperature is raised by at least 5° C. or more.

Next, as the secondary reaction, the formation and crystallization of dendritic precursor matrix of surface crystals, and removal or crystallization of the amorphous granule are carried out using calcium phosphate ion solution 4, followed by multiplication of the crystals adhered to the surface of the solid substrate, thereby preparing the ultrathin film of calcium phosphate crystals on the solid substrate. Here, it is desirable that the reaction rate be lowered by lowering the reaction temperature as much as possible to control crystallization rate. However, if the reaction temperature is too low, the reaction rate becomes too low. The reaction temperature may be set to be freezing point~50° C., preferably to be 5~35° C., and more preferably to be 10~25° C. for a proper reaction rate.

In both embodiments of the present invention, since the ultrathin film of calcium phosphate crystals has a very small thickness of 200 nm or less, it can coat the surface of the solid substrate while substantially maintaining a fine surface structure of the solid substrate.

According to the present invention, the solid substrate has a surface that is provided to prepare the ultrathin film of calcium phosphate and may be hydrophilic or hydrophobic. Preferably, the solid substrate may be organic polymer, metal, ceramics, glass, living tissues of animals or plants, etc. The organic polymer may be natural or synthetic polymers, and includes, but is not limited to, polystyrene, polycarbonate, polyglycolic acid, polylactic acid, poly lactic glycolitic acid, and the like. The metal may be any solid metal, and preferably, titanium is used in the case of a biomaterial. At this time, the material used as the solid substrate may have any geometrical shape. Accordingly, the solid substrate may have a variety of shapes including a planar shape, a cylindrical shape, a cubic shape, a cone shape, a prism shape, and combinations thereof. The solid substrate may be electrically charged or not.

Advantageous Effects

As apparent from the above description, the ultrathin film of calcium phosphate according to the present invention has a thickness of 200 nm or less and can be prepared using calcium phosphate ion solutions that can be simply prepared.

Further, the ultrathin film of calcium phosphate can be coated on the surface of a target material without negating a surface morphology of the target material.

Therefore, the ultrathin film of calcium phosphate according to the present invention can be coated on the surfaces of various solid substrates for various applications including biomaterials, adsorption of heavy metal ions, deodorization, adsorption of microorganisms such as viruses, and the like.

DESCRIPTION OF DRAWINGS

In FIG.7B, where small an amorphous granule is formed at a high density and crystallized at a high rate on a solid substrate such as metal, the ultrathin film of calcium phosphate crystals is prepared by forming an amorphous granule from which a crystalline extension is formed to remove the amorphous granule in step 1, and slowly growing the crystalline extension in step 2. If the reaction rate is not lowered in step 2, the growth of the crystalline extension is not adjusted, thereby forming a thick crystalline film.

BEST MODE

Figure 1:
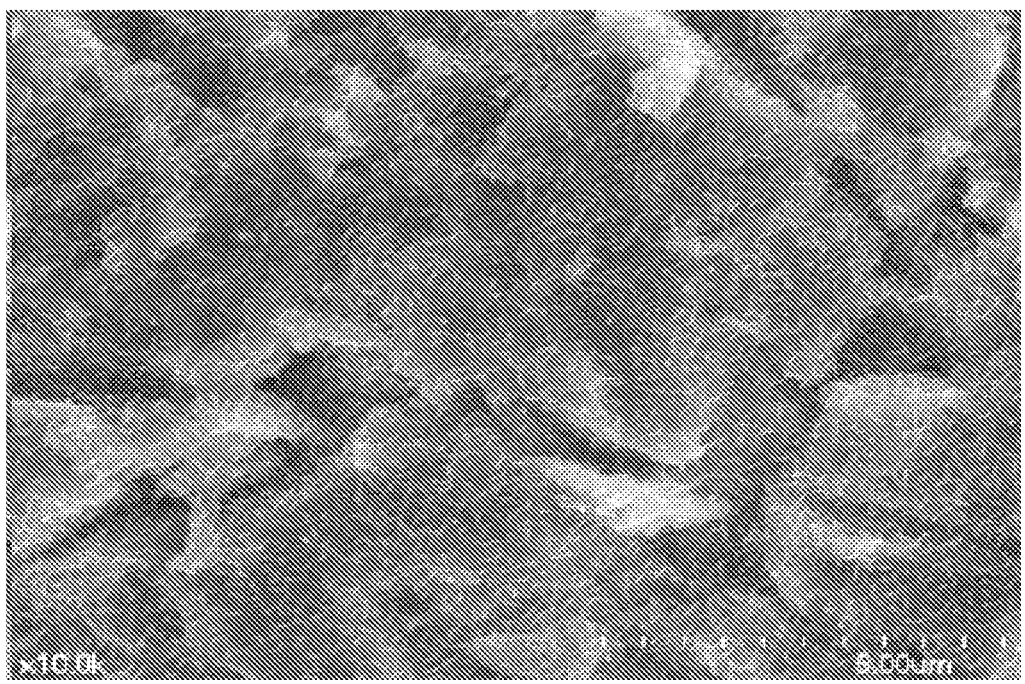
FIG. 1 is an SEM (scanning electron microscope) image (×5,000) of an ultrathin film of calcium phosphate crystals formed on a Ti-solid substrate according to one embodiment of the present invention, in which irregularities on the surface of the Ti-solid substrate are excellently maintained in spite of coating the surface with calcium phosphate crystals.

Hereinafter, inventive and comparative examples will be described along with test results for understanding of the present invention. It should be noted that these examples are given by way of illustration only and do not limit the scope of the present invention.

1. Preparation of a Calcium phosphate ion solution

EXAMPLE 1

Preparation of Calcium Phosphate Ion Solution 1 Used for the Surface of a Polystyrene Substrate or for the Surface of a Titanium Substrate A calcium phosphate ion solution used for forming granules of amorphous calcium phosphate having a diameter of 20 nm or less on the surface of the titanium substrate having a high surface energy or for forming granules of amorphous calcium phosphate having a diameter of 400 nm or less on the surface of the polystyrene substrate having a low surface energy was prepared as follows. A phosphate buffer solution at a pH of 7.4 and having a phosphate concentration of 2.5 mM was prepared. Then, 200 µl of 250 mM $CaNO_3$ aqueous solution was stirred at a high rate and added at 200 µl per minute at 1.0° C. to 20 ml of the phosphate buffer solution such that a final calcium ion concentration was 2.5 mM. The prepared calcium phosphate ion solution was maintained at 1° C. before use thereof.

EXAMPLE 2

Preparation of Calcium Phosphate Ion Solution 1 Used for a Formvar Film

A calcium phosphate ion solution used for forming granules of amorphous calcium phosphate having a diameter of 400 nm or less on the surface of the formvar film having a low surface energy was prepared as follows. A phosphate buffer solution at a pH of 7.4 and having a 2.8 mM phosphate concentration was prepared. Then, 200 µl of 280 mM $CaNO_3$ aqueous solution was stirred at a high rate and added at 200 µl per minute at 1.0° C. to 20 ml of the phosphate buffer solution such that a final calcium ion concentration was 2.5 mM. The prepared calcium phosphate ion solution was maintained at 1° C. before use thereof.

EXAMPLE 3

Preparation of Calcium Phosphate Ion Solution 2

A calcium phosphate ion solution used for forming a dendritic precursor matrix of surface crystals around the granule of amorphous calcium phosphate adhered to the surfaces of polystyrene and formvar films having low surface energies was prepared as follows. A phosphate buffer solution at a pH of 7.4 and having a 3 mM phosphate concentration was prepared. Then, 200 µl of 300 mM $CaNO_3$ aqueous solution was stirred at a high rate and added at 200 µl per minute at 1.0° C. to 20 ml of the phosphate buffer solution such that a final calcium ion concentration was 3 mM. The prepared calcium phosphate ion solution was maintained at 1° C. before the use thereof.

EXAMPLE 4

Preparation of Calcium Phosphate Ion Solution 3

A calcium phosphate ion solution used for dissolving the granule of amorphous calcium phosphate adhered to the surfaces of polystyrene and formvar films having low surface energies without dissolving the dendritic precursor matrix of surface crystals was prepared as follows. A phosphate buffer solution at a pH of 7.4 and having a 0.8 mM phosphate concentration was prepared. Then, 200 µl of 80 mM $CaNO_3$ aqueous solution was stirred at a high rate and added at 200 µl per minute at 1.0° C. to 20 ml of the phosphate buffer solution such that a final calcium ion concentration was 0.8 mM. The prepared calcium phosphate ion solution was maintained at 1° C. before use thereof.

EXAMPLE 5

Preparation of Calcium Phosphate Ion Solution 4

A calcium phosphate ion solution used for crystallization of the dendritic precursor matrix of surface crystals and multiplication of crystals and for treating the amorphous granule of the small size on the surface having a high surface energy was prepared as follows. A phosphate buffer solution at a pH of 7.4 and having a 2.5 mM phosphate concentration was prepared. Then, 200 µl of 250 mM $CaNO_3$ aqueous solution was stirred at a high rate and added at 200 µl per minute at 1.0° C. to 20 ml of the phosphate buffer solution such that a final calcium ion concentration was 2.5 mM. The prepared calcium phosphate ion solution was maintained at 1° C. before use thereof.

2. Preparation of an ultrathin film of calcium phosphate

EXAMPLE 6

Preparation of an Ultrathin Film of Calcium Phosphate Crystals on a Surface of Titanium A titanium disc having a diameter of 25 mm was placed in a hydrophobic polystyrene dish having a diameter of 35 mm and was maintained at −20° C. for 15 minutes, followed by lowering the temperature. Then, the 2.5 mM pH 7.4 calcium phosphate ion solution prepared and maintained at 1° C. in Example 1 was poured in an amount of 5 ml into the polystyrene dish with the titanium disc disposed therein, and maintained in an incubator at 42° C. for 40 minutes. Then, the temperature was increased to thereby form a small granule of amorphous calcium phosphate on the surface of the titanium disc. Then, the pH 7.4 calcium phosphate ion solution prepared in Example 5 and having a 2.5 mM calcium ion concentration and a 2.5 mM phosphate concentration was poured in an amount of 5 ml into the polystyrene dish, in which the titanium disc having the granule of amorphous calcium phosphate formed on the surface thereof was disposed, and maintained in an incubator of 18° C. for 50 minutes, thereby forming an ultrathin film of calcium phosphate crystals having a thickness of 200 nm or less on the surface of the titanium disc via formation of a dendritic precursor matrix of surface crystals, crystallization, and multiplication. FIG. 1 is an SEM image of the surface of the ultrathin film of calcium phosphate crystals.

Figures 2, 2A:
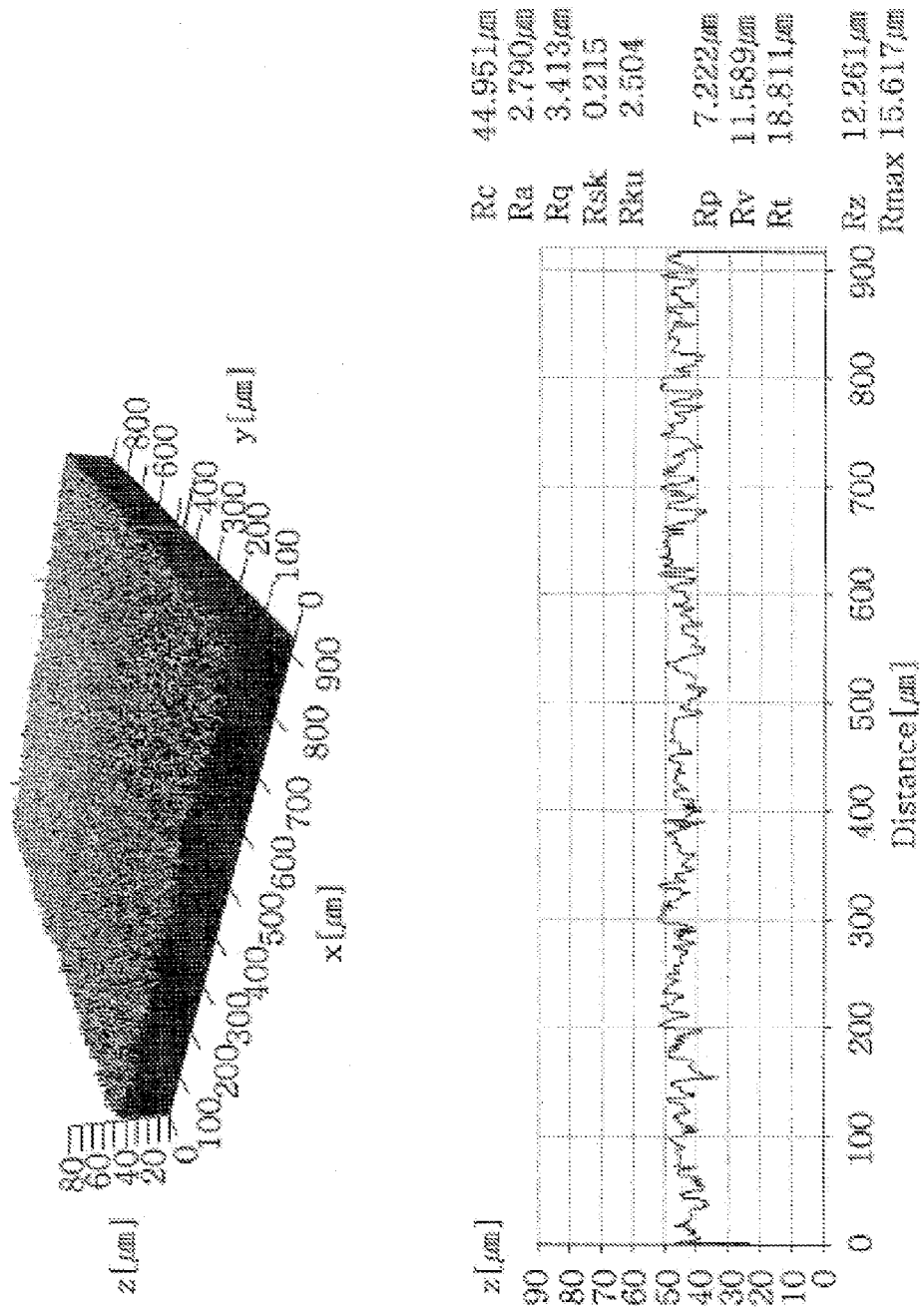
FIGS. 2A and 2B are graph depicting surface roughness (A: Ra=2.222 μm) of a Ti-solid substrate having an ultrathin film of calcium phosphate crystals formed thereon as an inventive example and a surface roughness (B: Ra=2.794 μm) of the Ti-solid substrate before forming the ultrathin film of the calcium phosphate crystals as measured using a confocal scanning microscope, showing that reduction in surface roughness is insignificant.
Figures 2, 2B:
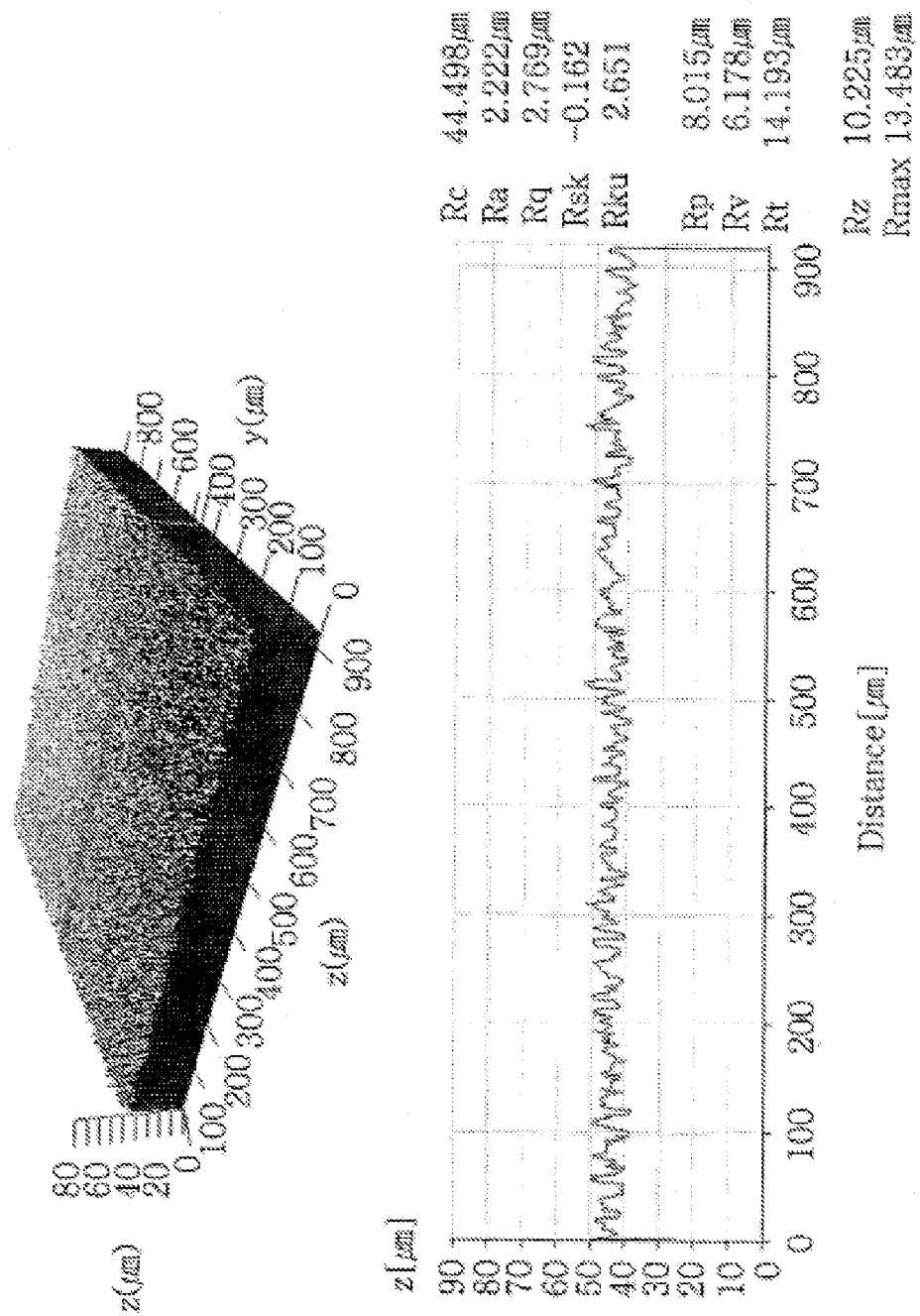

<Test 1> Measurement of Surface Roughness of the Ultrathin Film of Calcium Phosphate Crystals Formed on the Surface of the Titanium Disc The surface roughness of the titanium disc was compared with the surface roughness of the ultrathin film of calcium phosphate formed on the surface of the titanium disc using a confocal scanning microscope. FIG. 2 shows results of measuring the surface roughness. In FIG. 2, A shows the surface roughness after the ultrathin film of calcium phosphate was formed on the titanium surface, B shows the surface roughness before the formation of the ultrathin film. The surface of the titanium disc has a roughness Ra of 2.794 μm before the formation of the ultrathin film, and has a roughness Ra of 2.222 μm after the formation of the ultrathin film. From these results, it can be appreciated that the method of the present invention does not cause a significant reduction in the surface roughness. FIG. 2 is a graph depicting a surface roughness (A: Ra=2.222 μm) of a Ti-solid substrate having the ultrathin film of calcium phosphate crystals thereon and a surface roughness (B: Ra=2.794 μm) of the Ti-solid substrate before the formation of the ultrathin film as measured using the confocal scanning microscope.

COMPARATIVE EXAMPLE 1

Figure 3:
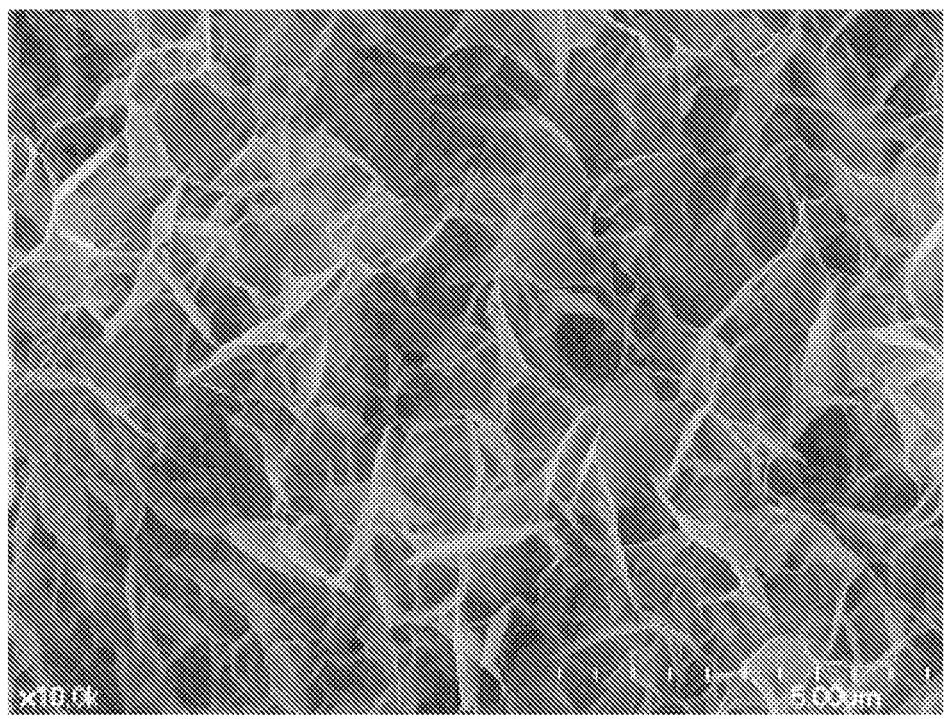
FIG. 3 is an SEM image of a thin film of calcium phosphate formed as a comparative example on a Ti-solid substrate by a conventional method, showing that the surface roughness of the Ti-solid substrate is significantly negated as compared to the surface of the Ti-solid substrate having the ultrathin film of calcium phosphate crystals formed thereon according to the embodiment of the present invention shown in FIG. 1.

Comparison with the Ultrathin Film of Calcium Phosphate Crystals Formed on the Surface of Titanium The ultrathin film of calcium phosphate crystals was prepared by the method of Example 6. Conversely, to prepare a typical thin film of calcium phosphate crystals, a titanium disc having a diameter of 25 mm was placed into a hydrophobic polystyrene dish having a diameter of 35 mm and was maintained at −20° C. for 15 minutes. Then, the temperature was lowered. Next, the 2.5 mM pH 7.4 calcium phosphate ion solution prepared and maintained at 1° C. in Example 1 was poured in an amount of 5 ml into the polystyrene dish with the titanium disc disposed therein, and maintained in an incubator of 42° C. for 70 minutes. Then, the temperature was increased to thereby form the thin film of calcium phosphate crystals on the surface of the titanium disc. FIG. 3 is an SEM image of the surface of the ultrathin film of calcium phosphate crystals. It can be appreciated from FIG. 3 that the fine surface roughness on the titanium substrate was negated by the thin film of calcium phosphate crystals.

EXAMPLE 7

Figure 4:
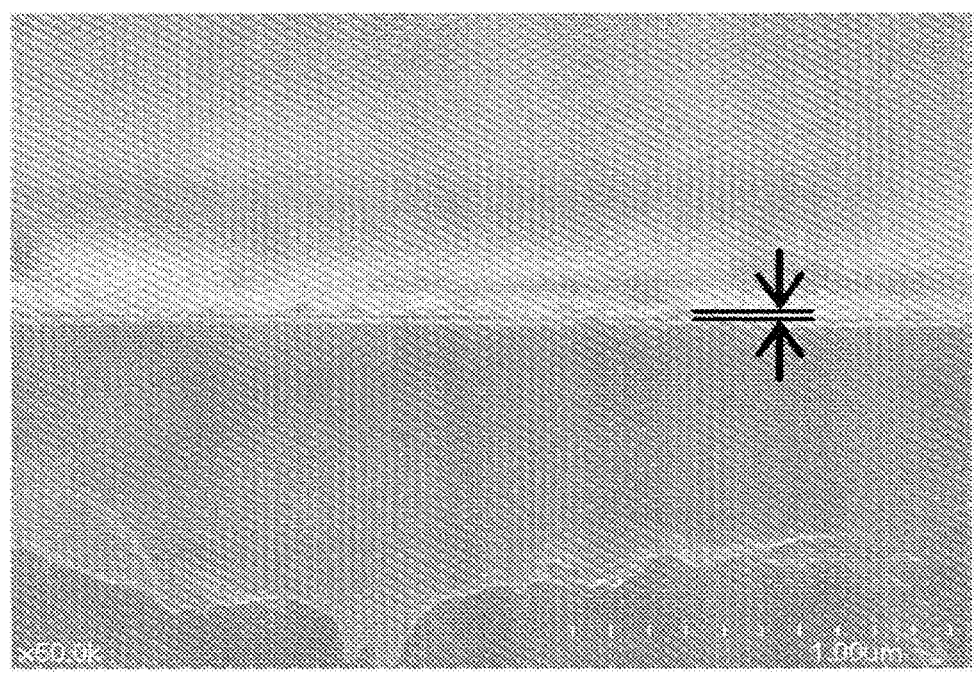
FIG. 4 is an SEM image (×5,000) showing a side of an ultrathin film of calcium phosphate crystals formed on a polystyrene solid substrate according to another embodiment of the present invention.

Preparation of an Ultrathin Film of Calcium Phosphate Crystals on a Surface of a Polystyrene Substrate A polystyrene dish having a diameter of 35 mm was maintained at −20° C. for 15 minutes, followed by lowering the temperature. Then, the 2.5 mM pH 7.4 calcium phosphate ion solution prepared and maintained at 1° C. in Example 1 was poured in an amount of 5 ml into the polystyrene dish and maintained in an incubator at 42° C. for 40 minutes. Then, the temperature was increased to thereby form granules of amorphous calcium phosphate having a size of 150~300 nm on the surface of the polystyrene dish. Then, a pH 7.4 calcium phosphate ion solution was prepared by the method of Example 3 to have a 3.0 mM calcium ion concentration and a 3.0 mM phosphate concentration, and poured in an amount of 5 ml into the polystyrene dish having the granule of amorphous calcium phosphate formed on the surface thereof, and maintained in an incubator at 18° C. for 2 hours, thereby forming dendritic amorphous precursor matrix of surface crystals composed of calcium phosphate having a low solubility on the surface of the polystyrene dish. Further, a pH 7.4 calcium phosphate ion solution was prepared by the method of Example 4 to have a 0.8 mM calcium ion concentration and a 0.8 mM phosphate concentration, poured in an amount of 5 ml into the polystyrene dish, and maintained in an incubator at 18° C. for 30 minutes to thereby leaving behind the dendritic precursor matrix of surface crystals composed of the amorphous calcium phosphate of the low solubility on the surface of the polystyrene dish while removing the amorphous granule having a high solubility. Then, a pH 7.4 calcium phosphate ion solution was prepared by the method of Example 5 to have a 2.5 mM calcium ion concentration and a 2.5 mM phosphate concentration, poured in an amount of 5 ml into the polystyrene dish, and maintained in an incubator of 18° C. for 50 minutes to treat the surface of the polystyrene dish again, thereby forming an ultrathin film of calcium phosphate having a thickness of 200 nm or less on the surface of the polystyrene dish. FIG. 4 is an SEM image of the surface of the ultrathin film of calcium phosphate crystals.

EXAMPLE 8

Figure 5:
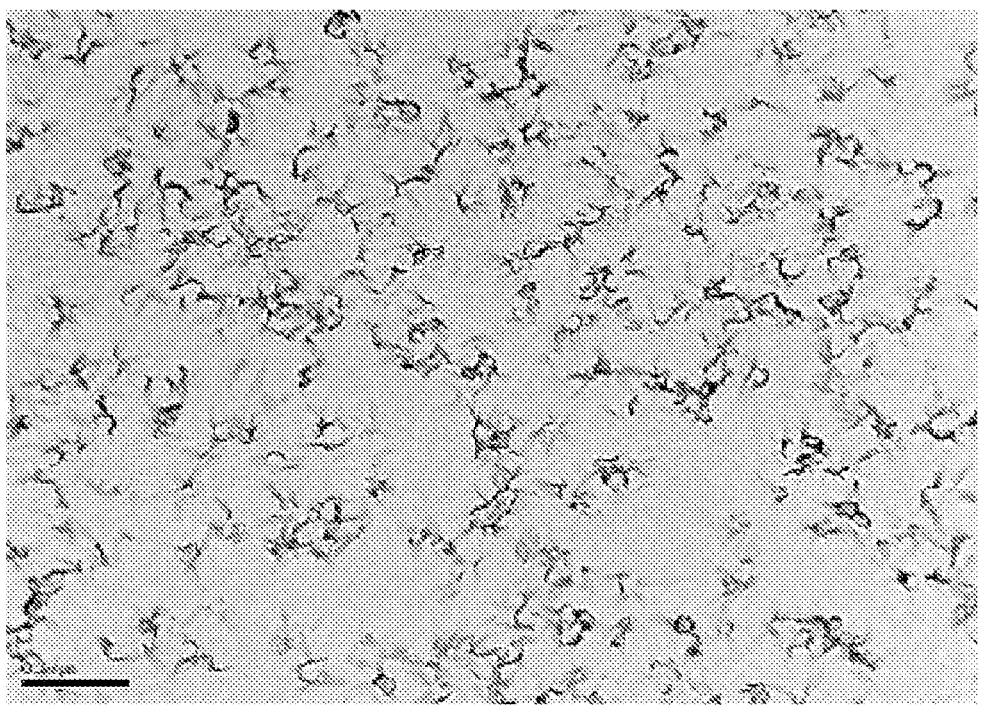
FIG. 5 is a TEM (transmission electron microscope) image (×50,000) of an ultrathin film of calcium phosphate crystals formed on a formvar solid substrate according to a further embodiment of the present invention.

Preparation of an Ultrathin Film of Calcium Phosphate Crystals on a Surface of a Formvar Film A polystyrene dish having a diameter of 35 mm was maintained at −20° C. for 15 minutes, followed by lowering the temperature. Then, the 2.8 mM pH 7.4 calcium phosphate ion solution prepared and maintained at 1° C. in Example 2 was poured in an amount of 5 ml into the polystyrene dish, and a formvar film-coated grid for a transmission electron microscope was floated on the solution and maintained in an incubator at 37° C. for 29 minutes. Then, the temperature was increased to thereby form granules of amorphous calcium phosphate having a size of 150~200 nm on the surface of the formvar film. Then, a pH 7.4 calcium phosphate ion solution prepared by the method of Example 3 to have a 3.0 mM calcium ion concentration and a 3.0 mM phosphate concentration was poured into the polystyrene dish, and the grid coated with the formvar film having the granule of amorphous calcium phosphate formed thereon was floated on the solution and reacted at 15° C. for 2 hours to thereby form a dendritic precursor matrix of surface crystals around the granule of amorphous calcium phosphate on the surface of the formvar film. Then, a pH 7.4 calcium phosphate ion solution prepared by the method of Example 4 to have a 0.8 mM calcium ion concentration and a 0.8 mM phosphate concentration was poured to treat the surface of the formvar film at 15° C. for 30 minutes, thereby allowing the dendritic precursor matrix of surface crystals having a low solubility on the surface of the formvar film to remain while removing the amorphous calcium phosphate. Then, a pH 7.4 calcium phosphate ion solution prepared by the method of Example 5 to have a 2.5 mM calcium ion concentration and a 2.5 mM phosphate concentration was poured to treat the surface of the formvar film at 15° C. for 30 minutes, thereby forming an ultrathin film of calcium phosphate crystals via crystallization and multiplication of the matrix. FIG. 5 is a TEM image of the ultrathin film of calcium phosphate crystals having a thickness of 200 nm or less. When such an ultrathin film of calcium phosphate crystals not covering the entire surface is applied to a biomaterial, cells and tissues can advantageously react with the solid substrate and the ultrathin film of calcium phosphate crystals at the same time.

3. Cell adhesion of an ultrathin film of calcium phosphate crystals

<Test 2> Test for Cell Adhesion of the Ultrathin Film of Calcium Phosphate Crystals A cell adhesion test was performed to examine biocompatibility of the ultrathin film of calcium phosphate crystals prepared in Example 6.

Osteoblast (MC3T3-E1 osteoblast, ATCC) was placed into a cell culture dish coated with the ultrathin film of calcium phosphate crystals prepared in Example 7, and incubated at 37° C. in a $CO_2$ constant temperature bath, into which 95% air and 5% carbon dioxide were supplied. After a day, the surface of the culture dish was observed using a phase contrast microscope (×200).

Figure 6:
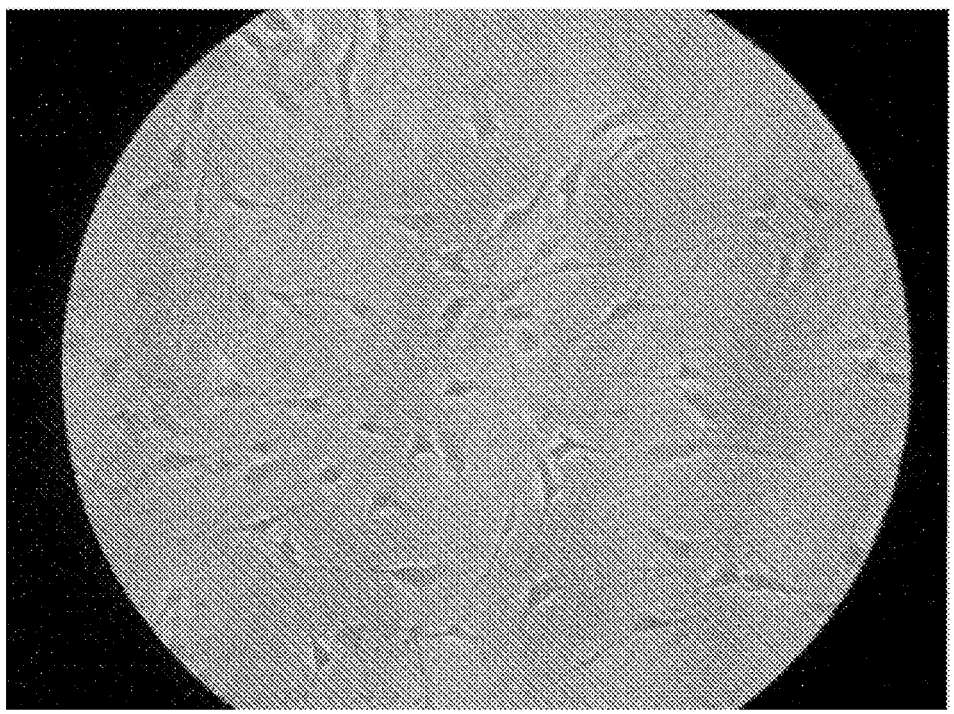
FIG. 6 is an optical microscope image (×200) of the ultrathin film of calcium phosphate crystals formed on the polystyrene solid substrate according to the embodiment of the present invention, in which cells are stably attached to the ultrathin film.
Figure 7:
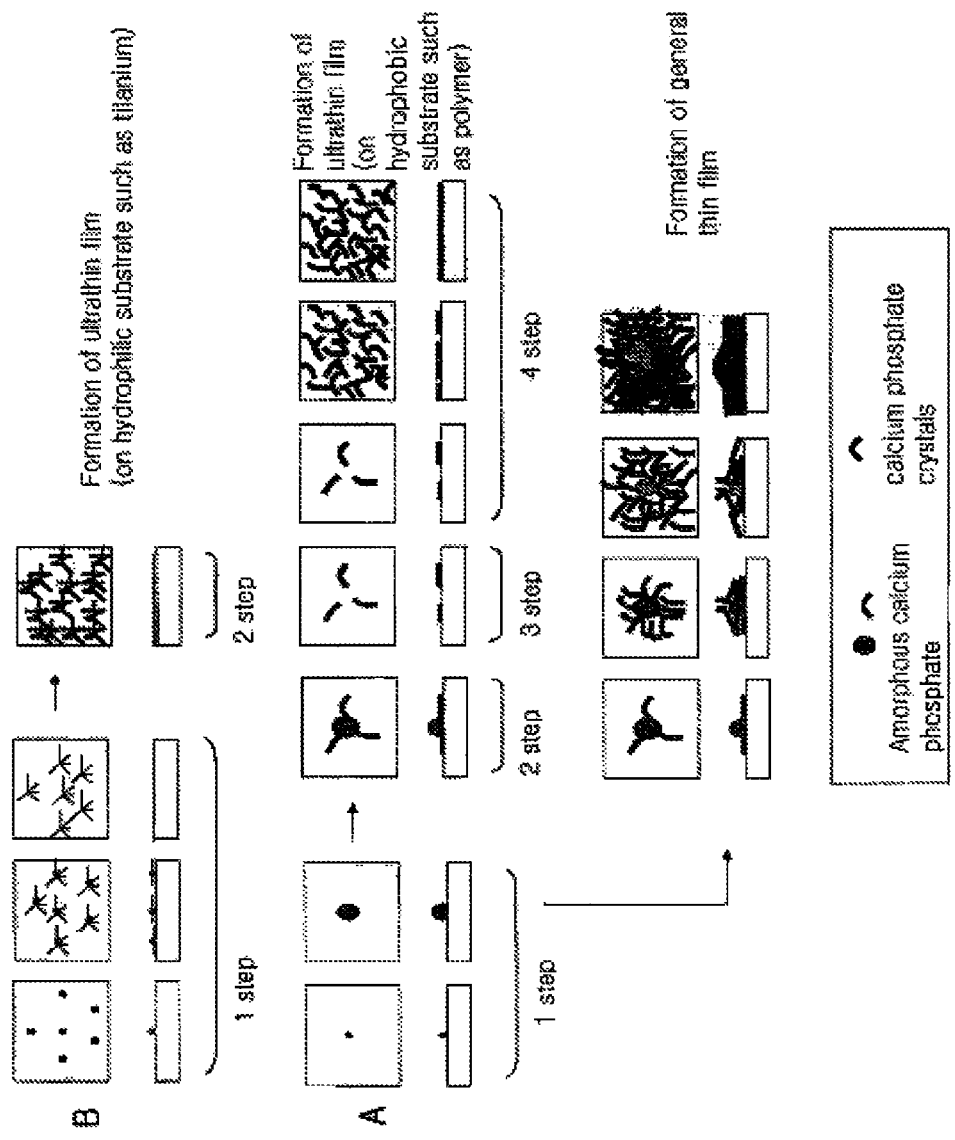
FIGS. 7A and 7B show diagrams illustrating preparation of an ultrathin film of calcium phosphate. Here, in FIG.7A, where an amorphous granule is formed at a low density and crystallized at a low rate on a hydrophobic surface such as a polymer, the ultrathin film of calcium phosphate crystals is prepared by forming an amorphous granule in step 1, forming an amorphous dendritic extension around the amorphous granule in step 2, dissolving the amorphous granule while allowing the amorphous dendritic extension to remain in step 3, and crystallizing and growing the dendritic extension in step 4. If a separate process is not performed after the formation of a small amorphous granule, calcium phosphate crystals are directly formed around a large amorphous granule, thereby forming a thick and rough calcium phosphate film.
Figure 8:
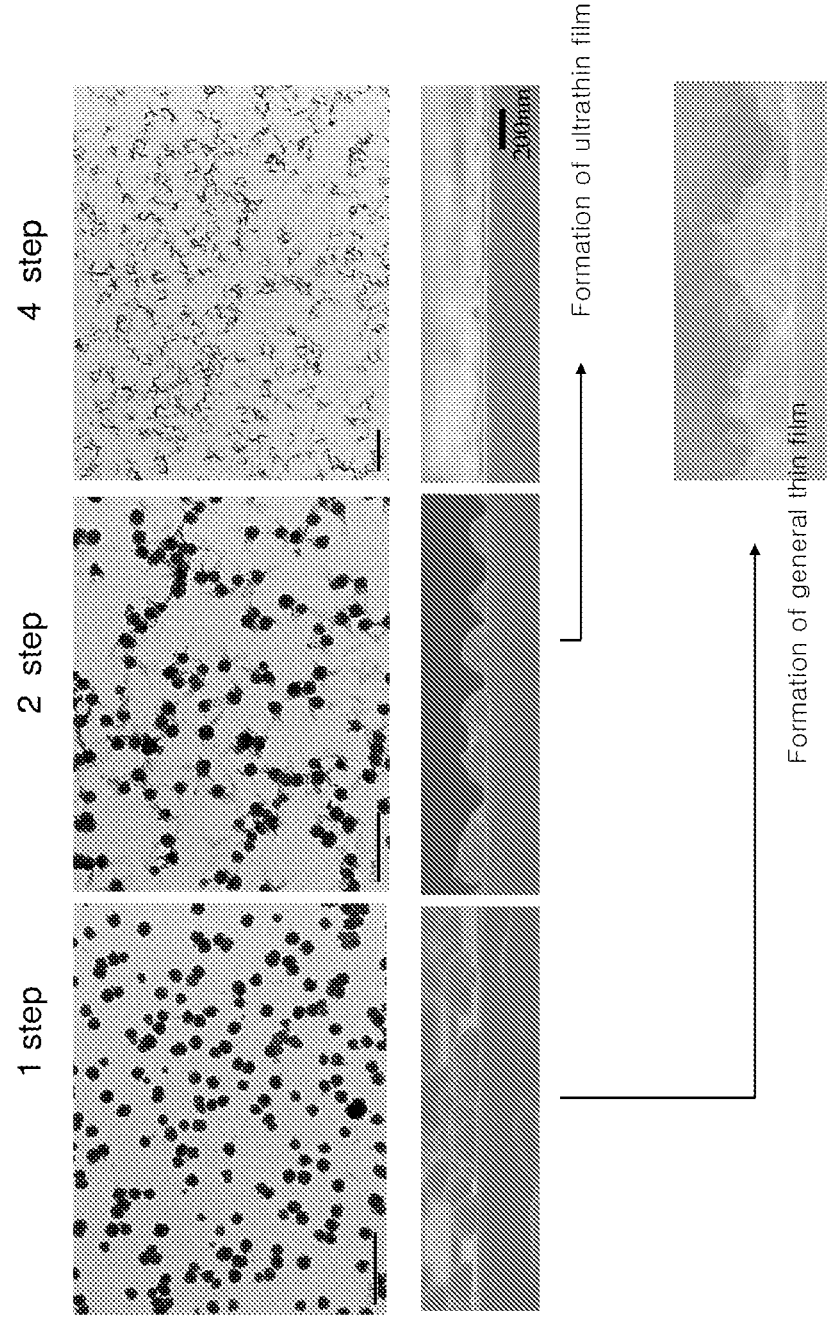
FIG. 8 is SEM images (upper side) and TEM images (lower side) in preparation of an ultrathin film on a polymer surface. Here, the ultrathin film is prepared by forming an amorphous granule in step 1, forming an amorphous dendritic extension around the amorphous granule in step 2, dissolving the amorphous granule while allowing the amorphous dendritic extension to remain in step 3, and crystallizing and growing the dendritic extension in step 4. If a separate process is not performed after the formation of the amorphous granule, calcium phosphate crystals are directly and thickly formed around a large amorphous granule, thereby forming a thick and rough calcium phosphate film.

As can been seen from FIG. 6, cells were stably attached to the ultrathin film of calcium phosphate crystals prepared in Example 7. Accordingly, it can be confirmed that the ultrathin film of calcium phosphate according to the present invention has good biocompatibility and thus can be used as a biomaterial.

The invention claimed is:

1. A method for producing ultrathin film of 200 nm or less thickness of calcium phosphate crystals on a solid substrate comprising:
   (1) contacting the substrate with a first calcium phosphate ion solution having an ion concentration product of 1~25 mM$^2$ [Ca$^{2+}$][PO4$^{3-}$], wherein temperature of the calcium phosphate ion solution is elevated by starting at a temperature range of 0~30° C. and finishing at a temperature range of 8~50° C., and temperature is raised by at least 5° C., so as to form granules of amorphous calcium phosphate on the substrate;
   (2) contacting the substrate on which is formed the granules of amorphous calcium phosphate obtained in step (1) with a second calcium phosphate ion solution so as to form amorphous dendritic extensions from said granules of amorphous calcium phosphate on the substrate;
   (3) contacting the substrate on which is formed the granules of amorphous calcium phosphate and the amorphous dendritic extensions from the granules of amorphous calcium phosphate obtained in step (2) with a third calcium phosphate ion solution so as to remove the granules of amorphous calcium phosphate and leave behind the amorphous dendritic extensions from the granules of amorphous calcium phosphate; and
   (4) contacting the substrate on which remains the amorphous dendritic extensions from the granules of amorphous calcium phosphate obtained in step (3) with a fourth calcium phosphate ion solution so as to crystallize the amorphous dendritic extensions into calcium phosphate crystals and multiply the calcium phosphate crystals to coat the substrate with the calcium phosphate crystals.

2. The method according to claim 1, wherein said second calcium phosphate ion solution of step 2 has an ion concentration product of 1~25 mM$^2$ [Ca$^{2+}$][PO4$^{3-}$] at a temperature of freezing point ~50° C.

3. The method according to claim 1, wherein said third calcium phosphate ion solution of step 3 has an ion concentration product of 0.16~1 mM$^2$ [Ca$^{2+}$][PO4$^{3-}$] at a temperature of freezing point ~50° C.

4. The method according to claim, wherein said fourth calcium phosphate ion solution of step 4 has an ion concentration product of 1~64 mM$^2$ [Ca$^{2+}$][PO4$^{3-}$] at a temperature of 5~50° C.

5. The method according to claim 1, wherein thickness of the calcium phosphate thin film on the substrate is 20 nm or less.

6. The method according to claim 1, wherein the substrate has hydrophobic or hydrophilic surface.

7. The method according to claim 6, wherein the substrate has hydrophobic surface.

8. The method according to claim 2, wherein said second calcium phosphate ion solution of step 2 has an ion concentration product of 1~25 mM$^2$ [Ca$^{2+}$][PO4$^{3-}$] at a temperature of freezing point of 5~35° C.

9. The method according to claim 8, wherein said second calcium phosphate ion solution of step 2 has an ion concentration product of 1~25 mM$^2$ [Ca$^{2+}$][PO4$^{3-}$] at a temperature of freezing point of 10~25° C.

10. The method according to claim 3, wherein said third calcium phosphate ion solution of step 3 has an ion concentration product of 0.16~1 mM$^2$ [Ca$^{2+}$][PO4$^{3-}$] at a temperature of freezing point of 5~35° C.

11. The method according to claim 10, wherein said third calcium phosphate ion solution of step 3 has an ion concentration product of 0.16~1 mM$^2$ [Ca$^{2+}$][PO4$^{3-}$] at a temperature of freezing point of 10~25° C.

12. The method according to claim 4, wherein said fourth calcium phosphate ion solution of step 4 has an ion concentration product of 1~64 mM$^2$ [Ca$^{2+}$][PO4$^{3-}$] at a temperature of 5~35° C.

13. The method according to claim 12, wherein said fourth calcium phosphate ion solution of step 4 has an ion concentration product of 1~64 mM$^2$ [Ca$^{2+}$][PO4$^{3-}$] at a temperature of 10~25° C.

14. The method according to claim 6, wherein the substrate has hydrophilic surface.

* * * * *